United States Patent [19]

Clitherow

[11] 4,394,516
[45] Jul. 19, 1983

[54] PROCESS FOR THE PREPARATION OF A FURAN DERIVATIVE

[75] Inventor: John W. Clitherow, Sawbridgeworth, England

[73] Assignee: Glaxo Group Limited, London, England

[21] Appl. No.: 375,963

[22] Filed: May 7, 1982

[30] Foreign Application Priority Data

May 7, 1981 [GB] United Kingdom ............... 8113944

[51] Int. Cl.³ ............................................. C07D 307/52
[52] U.S. Cl. ...................................... 549/495; 564/500
[58] Field of Search ........................................ 549/495

[56] References Cited

U.S. PATENT DOCUMENTS 4,128,658 12/1975 Price et al. ........................ 424/285
4,157,340 6/1979 Crenshaw et al. ............... 260/551 C

FOREIGN PATENT DOCUMENTS 2035313 6/1980 United Kingdom .

Primary Examiner—Richard Raymond
Attorney, Agent, or Firm—Bacon & Thomas

[57] ABSTRACT

Ranitidine is prepared by reacting cystamine of formula (II)

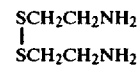

either with a nitroethenamine of formula (III)

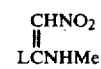

where L is a leaving group such as alkylthio, e.g. methylthio, or with a compound of formula (IV)

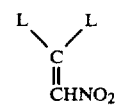

where L is a leaving group as defined above, followed by reaction with methylamine, to give a disulphide of formula (V)

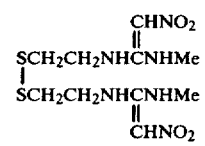

which is then reacted with 5-[(dimethylamino)methyl]-2-furanmethanol under acid conditions.

9 Claims, No Drawings

PROCESS FOR THE PREPARATION OF A FURAN DERIVATIVE

This invention relates to a process for the preparation of a furan derivative.

The furan derivative of formula (I)

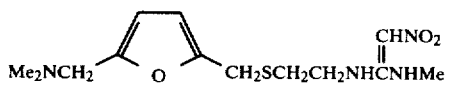
(I)

which is known as ranitidine is disclosed in British Patent Specification No. 1565966 as a potent and selective $H_2$-antagonist.

The present invention provides a process for the preparation of ranitidine of formula (I) which comprises reacting cystamine of formula (II)

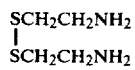
(II)

either with a nitroethenamine of formula (III)

(III)

where L is a leaving group such as alkylthio, e.g. methylthio, or with a compound of formula (IV)

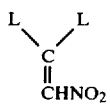
(IV)

where L is a leaving group as defined above, followed by reaction with methylamine, to give a disulphide of formula (V)

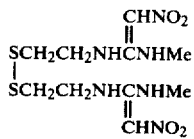
(V)

which is then reacted with 5-[(dimethylamino)methyl]-2-furanmethanol.

The reaction of the disulphide (V) with 5-](dimethylamino)methyl]-2-furanmethanol is carried out under acid conditions and conveniently at a temperature within the range 0°-100° C. Suitable acids include mineral acids such as hydrochloric or sulphuric acid, hydrochloric acid being preferred. More preferably the reaction is carried out in the presence of concentrated hydrochloric acid, conveniently at an initial temperature of 0°-4° C. with subsequent heating for a short period at for example 90°-100° C. Alternatively the reaction may be carried out in the presence of aqueous acid e.g. 5 M hydrochloric acid or 5 N sulphuric acid, preferably with heating e.g. at a temperature in the range of 35°-50° C.

In the preparation of the intermediate disulphide (V) cystamine is preferably reacted with the nitroethenamine of formula (III). This reaction may be carried out in the presence of a solvent such as acetonitrile or more preferably water, and conveniently at a temperature within the range of 0° to room temperature. Alternatively cystamine may be reacted with a compound of formula (IV) under the conditions described above, followed by reaction with methylamine at a temperature from ambient to reflux, preferably at room temperature.

Cystamine may conveniently be generated in situ from a salt such as the dihydrochloride for example by reaction with a base such as potassium hydroxide.

When L in the compounds of formulae (III) or (IV) is alkylthio it is desirable to pass a steady stream of a gas, such as nitrogen or air, through the reaction vessel during preparation of the disulphide.

If desired the furan derivative of formula (I) once obtained may be converted into an acid addition salt, e.g. a hydrochloride, using conventional methods. Thus for example appropriate quantities of the free base of formula (I) and an acid, e.g. hydrochloric acid, may be mixed in a suitable solvent(s), e.g. an alcohol such as ethanol, or an ester such as ethyl acetate.

The process of the present invention is advantageous in that it uses cheap and readily available starting materials, and the intermediate disulphide may be readily isolated in pure crystalline form.

The invention is illustrated by the following Examples.

EXAMPLE 1

N-[2-[[5-[(Dimethylamino)methyl]-2-furanylmethyl]thio]ethyl]-N'-methyl-2-nitro-1,1-ethenediamine (a) N,N'-bis-[Thio(2,1-ethanediyl)]bis(N'-methyl-2-nitro-1,1-ethenediamine)

To a stirred solution of 2,2'-dithiobisethanamine dihydrochloride (6.75 g) and potassium hydroxide (3.37 g) in water (150 ml) at 0°-4° was added finely powdered N-methyl(1methylthio)-2-nitroethenamine (8.98 g). A rapid stream of air was passed through the ice cold mixture for 2 h and for a further 2 h after the mixture had reached room temperature. The white precipitate which separated was filtered, washed with water then ethanol and ether and dried to give the title compound (8.53 g), m.p. 205°-207° decomp.

Found: C, 34.3; H, 5.7; N, 23.3. $C_{10}H_{20}N_6O_4S_2$ requires: C, 34.1; H, 5.7 N, 23.8%.

(b)
N-[2-[[5-[(Dimethylamino)methyl]-2-furanylmethyl]thio]ethyl]-N'-methyl-2-nitro-1,1-ethenediamine To a solution of 5-[(dimethylamino)methyl]-2-furanmethanol (1.72 g) in 5 M hydrochloric acid (2.2 ml) at room temperature was added N,N'-bis[thio(2,1-ethanediyl)] bis(N'-methyl-2-nitro-1,1-ethenediamine) (1.76 g) and 5 M hydrochloric acid (10 ml). After heating at 40°-45° for 23.5 h, tetrahydrofuran (120 ml) and excess anhydrous sodium carbonate was added. The mixture was stood at room temperature for 25.5 h then filtered and the filtrate evaporated in vacuo to give an oil (2.8 g). This was chromatographed on silica using methanol—0.88 ammonia, 200:1 and the appropriate eluate evaporated in vacuo to give an oil (0.37 g). The solid which separated on crystallisation from 4-methylpentan-2-one was filtered, washed with 4-methylpentan-2-one, isopropyl acetate and ether to give the title compound (0.09 g), m.p. 67.5°-69° which was not depressed on admixture with a sample prepared according to the method of Example 15 in British Patent Specification No.: 1565966.

EXAMPLE 2

N-[2-[[5-[(Dimethylamino)methyl]-2-furanylmethyl]thio]ethyl]-N'-methyl-2-nitro-1,1-ethenediamine To a stirred solution of N,N'-bis[thio(2,1-ethanediyl)]bis(N'-methyl-2-nitro-1,1-ethenediamine) (1.76 g) in concentrated hydrochloric acid (12 ml) cooled in ice was added 5-[(dimethylamino)methyl]-2-furanmethanol (1.72 g). The mixture was kept at 0°–4° for 64.5 hours and a further quantity of 5-[(dimethylamino)methyl]-2-furanmethanol (1.4 g) added. The mixture was heated at 98°–100° for 15 min. and the solution neutralised with sodium bicarbonate. Excess of anhydrous sodium carbonate and tetrahydrofuran (100 ml) were added and after 3 hours, the mixture was filtered and the filtrate evaporated in vacuo to give a dark oil. This oil was dissolved in 2-methylpentane-2-one (15 ml), the decolourising charcoal added, before the solution was heated to 98°–100° and filtered. The filtrate was evaporated in vacuo and the oily residue was mixed with water (10 ml) at 60°. The mixture was treated with decolourising charcoal and the solution filtered. The filtrate was evaporated to dryness in vacuo to give an oil (0.73 g) consisting of the title compound.

T.L.C Silica; methanol: 0.88 ammonia (200:1) $R_f$ 0.45 Consistent with a sample prepared according to the method of Example 15 in British Patent Specification No. 1565966.

I claim:

1. A process for the preparation of ranitidine of formula (I)

which comprises reacting cystamine of formula (II)

either with a nitroethenamine of formula (III)

where L is a leaving group, or with a compound of formula (IV)

where L is a leaving group, followed by reaction with methylamine, to give a disulphide of formula (V)

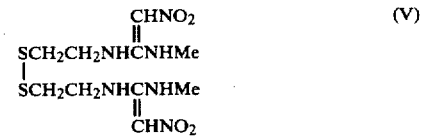

which is then reacted with 5-[(dimethylamino)methyl]-2-furanmethanol under acid conditions.

2. A process as claimed in claim 1 wherein the reaction between the disulphide (V) and 5-[(dimethylamino)methyl]-2-furanmethanol is carried out at a temperature of 0°–100° C.

3. A process as claimed in claim 2 wherein the reaction between the disulphide (V) and 5-[(dimethylamino)methyl]-2-furanmethanol is carried out in the presence of hydrochloric acid.

4. A process as claimed in claim 3 wherein the reaction is carried out in the presence of concentrated hydrochloric acid at an initial temperature of 0°–4° C., with subsequent heating for a short period at 90°–100° C.

5. A process as claimed in claim 1 wherein the disulphide (V) is prepared by reaction of cystamine and a nitroethenamine of formula (III) and this reaction is carried out in the presence of a suitable solvent.

6. A process as claimed in claim 5, wherein the solvent is water.

7. A process as claimed in claim 1 wherein L in the compounds of formulae (III) or (IV) is alkylthio and a steady stream of gas is passed through the reaction vessel during preparation of the disulphide.

8. A process as claimed in claim 1 in which the compound of formula (I) is converted into an acid addition salt.

9. A process as claimed in claim 8 in which the acid addition salt is the hydrochloride.

* * * * *